United States Patent
Kolman et al.

(10) Patent No.: US 11,111,219 B2
(45) Date of Patent: Sep. 7, 2021

(54) POLYSUBSTITUTED PYRIMIDINES INHIBITING THE FORMATION OF PROSTAGLANDIN E2, A METHOD OF PRODUCTION THEREOF AND USE THEREOF

(71) Applicants: USTAV ORGANICKE CHEMIE A BIOCHEMIE AV CR, V.V.I., Prague (CZ); USTAV EXPERIMENTALNI MEDICINY AV CR, V.V.I., Prague (CZ)

(72) Inventors: Viktor Kolman, Prague (CZ); Filip Kalcic, Karlovy Vary (CZ); Zlatko Janeba, Prague (CZ); Zdenek Zidek, Prague (CZ)

(73) Assignee: USTAV ORGANICKE CHEMIE A BIOCHEMIE AV CR, V.V.I., Prague (CZ)

( * ) Notice: Subject to any disclaimer, the term of this patent is extended or adjusted under 35 U.S.C. 154(b) by 0 days.

(21) Appl. No.: 16/612,585

(22) PCT Filed: May 23, 2018

(86) PCT No.: PCT/CZ2018/050024
§ 371 (c)(1),
(2) Date: Nov. 11, 2019

(87) PCT Pub. No.: WO2018/215003
PCT Pub. Date: Nov. 29, 2018

(65) Prior Publication Data
US 2020/0199080 A1    Jun. 25, 2020

(30) Foreign Application Priority Data
May 24, 2017   (CZ) ................. CZ2017-293

(51) Int. Cl.
*A61K 31/505* (2006.01)
*A61P 29/00* (2006.01)
*C07D 239/42* (2006.01)

(52) U.S. Cl.
CPC .................. *C07D 239/42* (2013.01)

(58) Field of Classification Search
CPC ... A61K 31/505; A61K 2121/00; A61P 29/00; C07D 239/42
See application file for complete search history.

(56) References Cited

U.S. PATENT DOCUMENTS 8,883,798 B2    11/2014   Jansa et al.

FOREIGN PATENT DOCUMENTS

WO    2012116666 A1    9/2012

OTHER PUBLICATIONS

Nicklas Deibl et al, "Sustainable Multicomponent Pyrimidine Synthesis", Journal of the American Chemical Society, vol. 137, No. 40, Oct. 1, 2015 (Oct. 1, 2015), pp. 12804-12807.
International Search Report and Written Opinion for corresponding PCT/CZ2018/050024, dated Aug. 6, 2018.

*Primary Examiner* — Brenda L Coleman
(74) *Attorney, Agent, or Firm* — Notaro, Michalos & Zaccaria P.C.

(57) ABSTRACT

The invention describes the pyrimidine-based compounds of the general formula I. Described compounds lower the production of the prostaglandin $E_2$. In concentrations lowering production of this factor by 50%, these compounds have no negative effect on the cell viability and they are not cytotoxic. Furthermore, the method of production of the compounds of the general formula I is provided. A pharmaceutical composition comprising the polysubstituted pyrimidines according to the invention and the use of these compounds for the treatment of the inflammatory diseases are also provided.

3 Claims, 1 Drawing Sheet

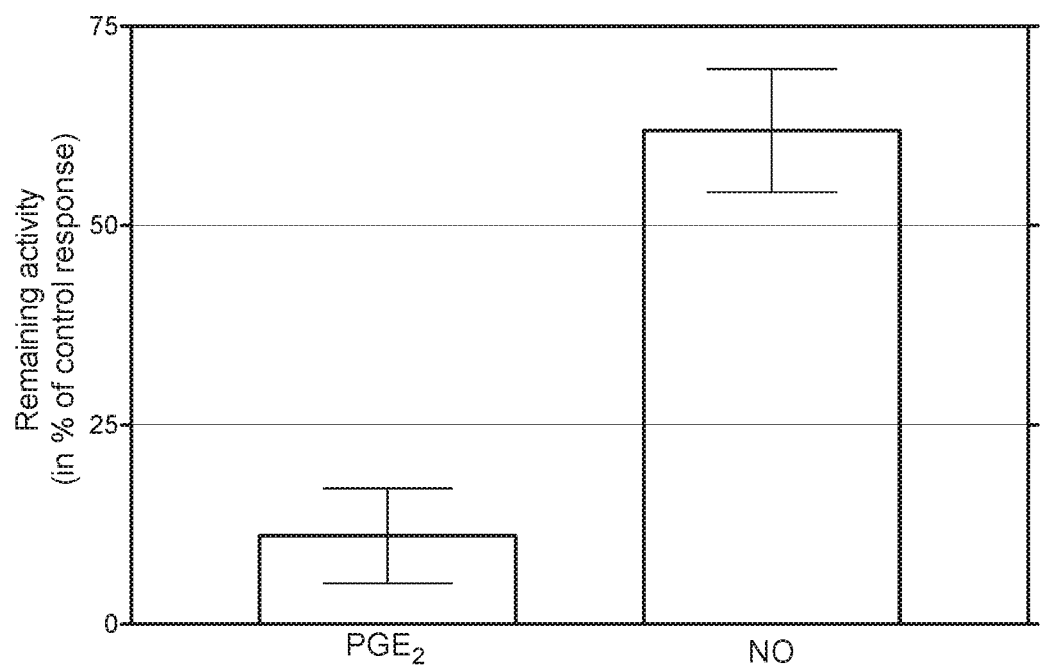

POLYSUBSTITUTED PYRIMIDINES INHIBITING THE FORMATION OF PROSTAGLANDIN E2, A METHOD OF PRODUCTION THEREOF AND USE THEREOF

FIELD OF THE INVENTION

The present invention relates to polysubstituted pyrimidines and their usage as prostaglandin $E_2$ production inhibitors.

PRIOR ART

Prostaglandin $E_2$ ($PGE_2$) is a lipid-like prostanoid. It is biosynthesized via a cascade of enzymatic reactions from arachidonic acid (Park, J. Y., *Clin. Immunol.* 2006, 119, 229-240). During the normal state of the organism, the $PGE_2$ shows homeostatic properties. During the pathological state, the production of $PGE_2$ is induced via proinflammatory cytokines (e.g. interleukin-1β (IL-1β), tumor necrosis factor α (TNF-α) and interferon-γ (IFN-γ) (Dinarello, C. A., *Chest* 2000, 118, 503-508). As the consequence $PGE_2$ shows inflammatory properties.

Arachidonic acid is a substrate for enzyme cyclooxygenase (constitutive cyclooxygenase COX-1 and inducible COX-2). The COX transforms arachidonic acid into prostaglandin $H_2$ ($PGH_2$). The terminal enzyme in the process is microsomal prostaglandin $E_2$ synthase (mPGES-1). The mPGES-1 transforms the $PGH_2$ to $PGE_2$. Similarly to COX-2, the mPGES-1 is an inducible enzyme. Both COX-2 and mPGES-1 are induced by the same stimuli.

It has been shown that the proinflammatory factors (e.g. pain, swelling, fewer and redness) are lowered if the production of induced $PGE_2$ is inhibited. Commonly used $PGE_2$ production inhibitors are glucocorticoids, nonsteroidal anti-inflammatory drugs (NSAIDs, nonselective inhibitors of COX-1 and COX-2) and lately, so-called "coxibs" (selective COX-2 inhibitors). Unfortunately, all the above-mentioned strategies show severe side effects. The glucocorticoids are immunosuppressive, NSAIDs cause gastrointestinal tract damage and the "coxibs" cause cardiovascular issues. Therefore there is a dire need for the development of new $PGE_2$ production inhibitors with less or no side effects and possibly with a new mode of action.

Substituted pyrimidines show a wide range of biological activity (Sahu, M., *Int. J. Pharm. Pharm. Sci.* 2016, 8, 5, 8-21). From the literature, few examples are known of polysubstituted pyrimidines with anti-inflammatory properties. Pyrimidine substituted urea motives were used as inhibitors of proinflammatory cytokines TNF-α and interleukin-6 (Keche, A. P., *Bioorg. Med. Chem. Lett.* 2012, 22, 3445-3448). 2,4-Diamino-5-cyclopropylpyrimidines were published as inhibitors of TBK1/IKK$_{249}$ kinases regulating transcription processes related to the production of proinflammatory cytokines (McIver, *Bioorg. Med. Chem. Lett* 2012, 22, 7169-7173). Suitably substituted dihydropyrimidines were described as inhibitors of the mPGES-1, the key enzyme in the $PGE_2$ biosynthesis (Lauro, G., *Eur. J. Med. Chem* 2014, 80, 407-415). The pirinixic acid derivatives showed activity as dual inhibitors of mPGES-1 and 5-lipoxygenase (5-LO) (Hanke, T., *J. Med. Chem.* 2013, 56, 9031-9044).

In our laboratory, the polysubstituted pyrimidines were discovered, patented and lately published serving as dual inhibitors of production of $PGE_2$ and nitric oxide (NO) (Jansa, P. WO2012116666 2012, A1; U.S. Pat. No. 8,883,798); Jansa, P. *Med. Chem. Res.* 2014, 23, 4482-4490; Jansa, P. *Med. Chem. Res.* 2015, 24, 2154-2166).

DISCLOSURE OF THE INVENTION

The aspect of this invention is the polysubstituted pyrimidine compounds of general formula I,

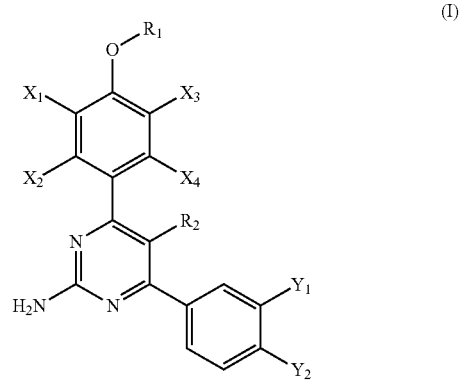

(I)

wherein $X_1$ to $X_4$ are the same or different substituents selected from the group consisting of —H, —F, —Cl, —OR, alkyl wherein R is hydrogen or a substituent selected from the group of alkyl, alkenyl, alkynyl and aryl as defined herein;

$Y_1$ and $Y_2$ are the same or different substituents selected from the group consisting of —H, —F, —Cl, —OR, —SR, —R, —CF$_3$ wherein R is hydrogen or a substituent selected from the group consisting of alkyl, alkenyl, alkynyl and aryl, as defined herein;

$R_1$ is a substituent selected from the group consisting of alkyl, alkenyl, alkynyl, aryl as defined herein, with the proviso that alkyl does not include methyl;

$R_2$ is alkyl as defined herein;

or a pharmaceutically acceptable salt thereof, wherein, alkyl in these cases is defined as a linear or branched $C_1$-$C_{10}$ carbon chain in which any —CH$_2$— group can be replaced by a —O— or —S— substituent;

alkenyl in these cases is defined as a linear or branched $C_1$-$C_{10}$ carbon chain containing at least one double bond in which any —CH$_2$— group can be replaced by a —O— or —S— substituent;

alkynyl in these cases is defined as a linear or branched C1-C10 carbon chain containing at least one triple bond in which any —CH$_2$— group can be replaced by a —O— or —S— substituent;

aryl in the above cases is defined as a hydrocarbon group containing 6 to 14 carbon atoms containing at least one aromatic ring wherein the aryl may be unsubstituted or substituted with 1 to 5 substituents selected from the group of —F, —Cl, —OR, alkyl, wherein R is hydrogen or a substituent selected from the group consisting of alkyl, alkenyl, or alkynyl as defined herein.

More preferably, the invention relates to the following polysubstituted pyrimidines of the general formula I:

5-butyl-4-(4-ethoxyphenyl)-6-phenylpyrimidin-2-amine,
5-butyl-4-(4-isopropoxyphenyl)-6-phenylpyrimidin-2-amine,
5-butyl-4-phenyl-6-(3,4,5-trimethoxyphenyl)pyrimidin-2-amine,
4-(4-(benzyloxy)phenyl)-6-phenylpyrimidin-2-amine, 4-(4-(benzyloxyphenyl)-5-butyl-6-phenylpyrimidin-2-amine,
5-butyl-4-(4-(naphthalen-1-ylmethoxy)phenyl)-6-phenylpyrimidin-2-amine,
4-(4((4-methoxybenzyl)oxy)phenyl)-6-phenylpyrimidin-2-amine,
5-butyl-4-(4-((4-methoxybenzyl)oxy)phenyl)-6-phenylpyrimidin-2-amine,
4-(4-(4-chlorobenzyl)oxy)phenyl)-6-phenylpyrimidin-2-amine,
5-butyl-4-(4-((4-chlorobenzyl)oxy)phenyl)-6-phenylpyrimidin-2-amine,
4-(4-(benzyloxy)-2-methylphenyl)-5-butyl-6-phenylpyrimidin-2-amine,
4-(4-(benzyloxy)-2,3-difluorophenyl)-6-phenylpyrimidin-2-amine,
4-(4-(benzyloxy)-2,3-difluorophenyl)-5-butyl-6-phenylpyrimidin-2-amine,
5-butyl-4-(4-((2-chlorobenzyl)oxy)-3,5-dimethylphenyl)-6-phenylpyrimidin-2-amine,
5-butyl-4-(4-((3-chlorobenzyl)oxy)-3,5-dimethylphenyl)-6-phenylpyrimidin-2-amine,
4-(4-(benzyloxy)phenyl)-5-butyl-6-(3-methoxyphenyl)pyrimidin-2-amine,
4-(4-(benzyloxy)phenyl)-5-butyl-6-(4-methoxyphenyl)pyrimidin-2-amine,
4-(4-(benzyloxy)phenyl)-5-butyl-6-(3-chlorophenyl)pyrimidin-2-amine,
4-(4-(benzyloxy)phenyl)-5-butyl-6-(4-chlorophenyl)pyrimidin-2-amine,
and their pharmaceutically acceptable salts.

As used herein, the term "pharmaceutically acceptable salts" refers to salts which are within reasonable medical judgment suitable for use in contact with the tissues of humans and lower animals without undue toxicity, irritation, allergic reactions, and the like, and have an acceptable benefit/risk ratio. Pharmaceutically acceptable salts are well known in the field, for example, P. H. Stahl and the coauthors described the pharmaceutically acceptable salts in detail in "Handbook of Pharmaceutical Salts Properties, Selection, and Use" (Wiley V C H, Zunch, Switzerland: 2002). Examples of such salts include but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, hydroxyethanesulfonate (isethionate), lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, phosphate, glutamate, bicarbonate, p-toluenesulfonate and undecanoate. Also groups containing a nitrogen atom can be quaternized with agents such as lower alkyl halides such as methyl, ethyl, propyl and butyl chlorides, bromides and iodides; dialkyl sulfates such as dimethyl, diethyl, dibutyl and diamyl sulfates, long chain halides such as decyl, lauryl, myristyl and stearyl chlorides, bromides and iodides; arylalkyl halides such as benzyl and phenethyl bromides and others.

The subject of the present invention are furthermore the polysubstituted pyrimidines of the formula I for use as pharmaceuticals.

The subject of the present invention is also the polysubstituted pyrimidines of formula I for use as drugs which inhibit the overproduction of prostaglandin $E_2$.

The subject of the present invention are also the polysubstituted pyrimidines of the formula I for use as medicaments for the treatment of diseases which are induced or their severity is increased by the overproduction of prostaglandin $E_2$, especially for the treatment of inflammatory and/or cancerous diseases or as anti-angiogenic, immunomodulatory, an antiproliferative or anticancer drug.

It is also a subject of the present invention to use a substituted pyrimidine of formula (I) as another active ingredient of a pharmaceutical composition for the treatment of diseases which are induced or their severity is increased by the overproduction of prostaglandin $E_2$, in particular for the treatment of inflammatory and/or tumor diseases.

The present invention also provides a pharmaceutical composition comprising a therapeutically effective amount of a compound of formula I and optionally at least one pharmaceutically acceptable carrier, filler and/or diluent.

The subject of the present invention also provides a pharmaceutical composition for use in the treatment of diseases which are induced or their severity is increased by the overproduction of prostaglandin $E_2$, in particular for the treatment of inflammatory and/or tumor diseases.

The term "therapeutically effective amount" as used herein refers to an amount of a compound or drug that is effective in "treating" a disease or disorder in a human or a mammal. In the case of cancer treatment, a therapeutically effective amount of a drug may reduce the number of cancer cells; reduce tumor size; inhibit (i.e., to some extent slow down and preferably stop) the infiltration of cancer cells into the peripheral organs; inhibit, to some extent, and preferably stop, the formation of tumor metastases, inhibit, to some extent, tumor growth and/or to some extent alleviate one or more symptoms associated with cancer. Since the drug can prevent growth and/or kill existing cancer cells, it may be cytostatic and/or cytotoxic.

The term "pharmaceutical composition" refers to the formulation of a compound and medium generally recognized in the art for delivery of a biologically active compound to a mammal, e.g., a human. Such a medium includes all pharmaceutically acceptable carriers, diluents or excipients.

The term "pharmaceutically acceptable carrier, diluent or filler" as used herein includes, without limitation, any excipient, carrier, glidant, sweetener, preservative, dye, flavor enhancer, surfactant, dispersing agent, suspending agent, isotonic agent, solvent, or emulsifier that has been approved for use in humans or domestic animals.

The invention further encompasses compounds of formula (I) for administration as a single active ingredient of a pharmaceutically acceptable composition which can be prepared by conventional methods known in the art, for example by binding the active ingredient to a pharmaceutically acceptable, therapeutically inert organic and/or inorganic carrier or excipient, or mixed therewith.

Another possibility is the use of a compound of formula (I) as a second or other active ingredient having a synergistic effect with other active ingredients in known drugs, or administration of the compounds of formula (I) together with such drugs.

The compounds of formula (I) of the present invention may also be used in the form of a prodrug or another suitably formulated form which releases the active ingredient in vivo.

The presented compounds of the general formula I differ from the previously published group of polysubstituted pyrimidines (Jansa, P. WO2012116666 2012, A1; U.S. Pat. No. 8,883,798). The previously published compounds acted as the dual inhibitors of $PGE_2$ and NO. They also lack the substitution on oxygen in position 4 of the C4-phenyl ring. This structural change leads to increased and selective inhibition of $PGE_2$ without showing the NO inhibition. Currently published compounds show no or low inhibition of NO production and thus cannot be considered as dual inhibitors.

BRIEF DESCRIPTION OF THE DRAWINGS

The FIGURE: Overall effects of tested pyrimidine derivatives on the production of PGE2 and NO by mouse peritoneal cells. The bars are means±95% limits of confidence averaged over effects of nineteen tested compounds.

EXAMPLES

LIST OF ABBREVIATION

DMSO dimethylsulfoxide
NMR nuclear magnetic resonance
HRMS high resolution mass spectrometry
EtOAc ethyl acetate
LPS lipopolysaccharide
LDH kit lactate dehydrogenase test kit The range of the invention is not limited by the following examples.

TABLE 1

Overview of the compounds prepared in following examples.

| Compound | | Structure | Nomenclature |
|---|---|---|---|
| 1 | 1a | 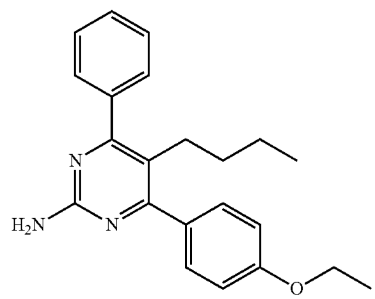 [SMILES: CCCCc1c(-c2ccccc2)nc(N)nc1-c1ccc(OCC)cc1] | 5-butyl-4-(4-ethoxyphenyl)-6-phenylpyrimidin-2-amine |
| 2 | 1b | 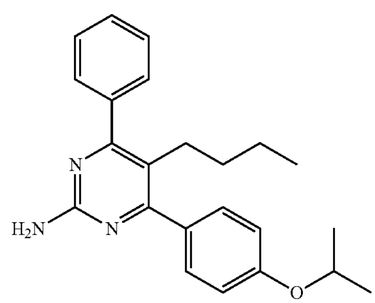 [SMILES: CCCCc1c(-c2ccccc2)nc(N)nc1-c1ccc(OC(C)C)cc1] | 5-butyl-4-(4-isopropoxyphenyl)-6-phenylpyrimidin-2-amine |
| 3 | 1c | 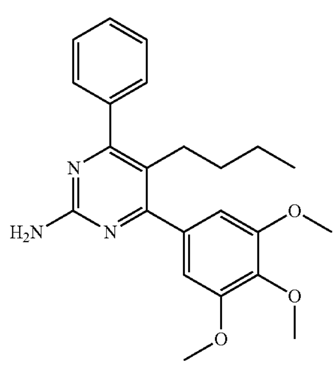 [SMILES: CCCCc1c(-c2ccccc2)nc(N)nc1-c1cc(OC)c(OC)c(OC)c1] | 5-butyl-4-phenyl-6-(3,4,5-trimethoxyphenyl)pyrimidin-2-amine |

TABLE 1-continued

Overview of the compounds prepared in following examples.

| | Compound | Structure | Nomenclature |
|---|---|---|---|
| 4 | 1d | 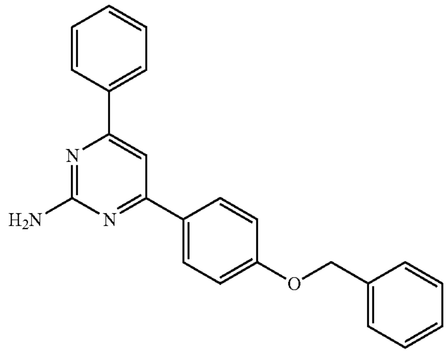 [SMILES: Nc1nc(-c2ccccc2)cc(-c2ccc(OCc3ccccc3)cc2)n1] | 4-(4-(benzyloxy)phenyl)-6-phenylpyrimidin-2-amine |
| 5 | 1e | 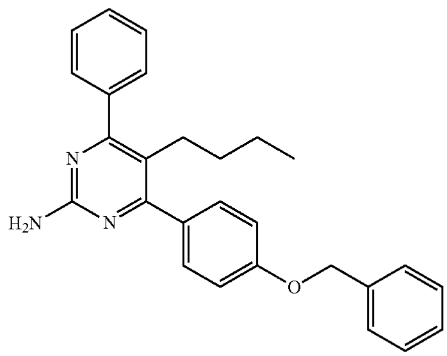 [SMILES: CCCCc1c(-c2ccccc2)nc(N)nc1-c1ccc(OCc2ccccc2)cc1] | 4-(4-(benzyloxy)phenyl)-5-butyl-6-phenylpyrimidin-2-amine |
| 6 | 1f | 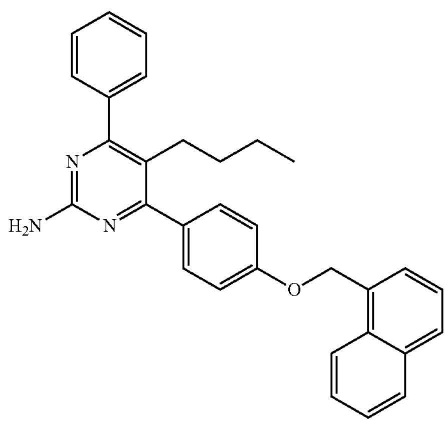 [SMILES: CCCCc1c(-c2ccccc2)nc(N)nc1-c1ccc(OCc2cccc3ccccc23)cc1] | 5-butyl-4-(4-(naphthalen-1-ylmethoxy)phenyl)-6-phenylpyrimidin-2-amine |
| 7 | 1g | 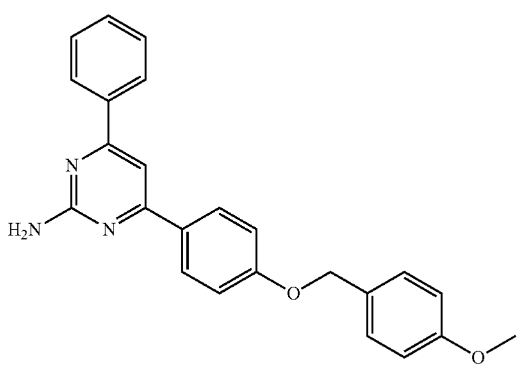 [SMILES: COc1ccc(COc2ccc(-c3cc(-c4ccccc4)nc(N)n3)cc2)cc1] | 4-(4-((4-methoxybenzyl)oxy)phenyl)-6-phenylpyrimidin-2-amine |

TABLE 1-continued

Overview of the compounds prepared in following examples.

| Compound | | Structure | Nomenclature |
| --- | --- | --- | --- |
| 8 | 1h | 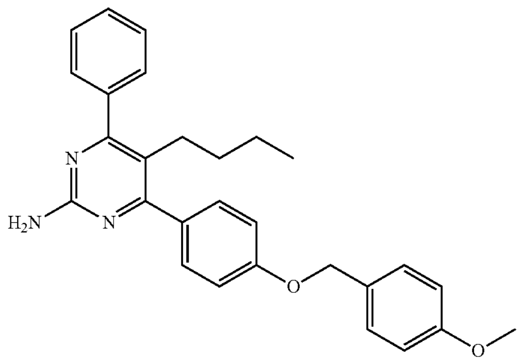 [SMILES: CCCCc1c(-c2ccccc2)nc(N)nc1-c1ccc(OCc2ccc(OC)cc2)cc1] | 5-butyl-4-(4-((4-methoxybenzyl)oxy)phenyl)-6-phenylpyrimidin-2-amine |
| 9 | 1i | 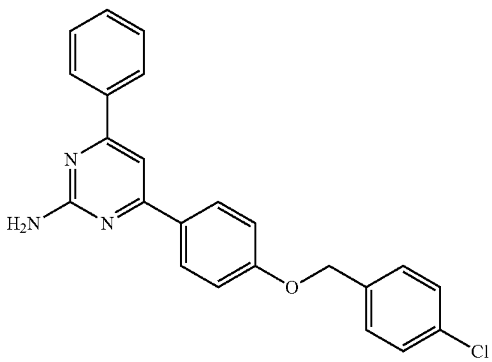 [SMILES: Nc1nc(-c2ccccc2)cc(-c2ccc(OCc3ccc(Cl)cc3)cc2)n1] | 4-(4-((4-chlorobenzyl)oxy)phenyl)-6-phenylpyrimidin-2-amine |
| 10 | 1j | 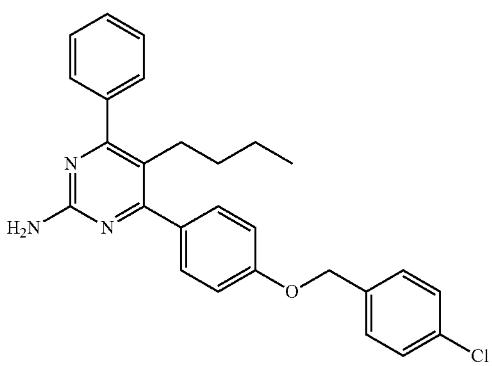 [SMILES: CCCCc1c(-c2ccccc2)nc(N)nc1-c1ccc(OCc2ccc(Cl)cc2)cc1] | 5-butyl-4-(4-((4-chlorobenzyl)oxy)phenyl)-6-phenylpyrimidin-2-amine |
| 11 | 1k | 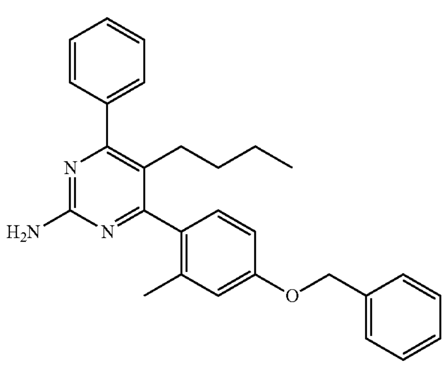 [SMILES: CCCCc1c(-c2ccccc2)nc(N)nc1-c1ccc(OCc2ccccc2)cc1C] | 4-(4-(benzyloxy)-2-methylphenyl)-5-butyl-6-phenylpyrimidin-2-amine |

TABLE 1-continued

Overview of the compounds prepared in following examples.

| Compound | | Structure | Nomenclature |
| --- | --- | --- | --- |
| 12 | 1l | 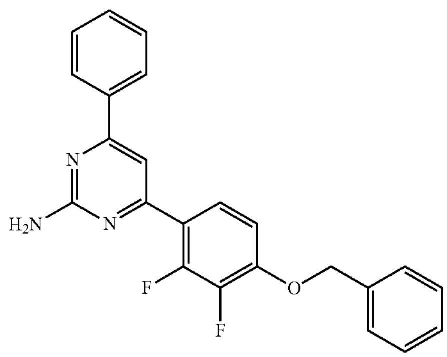 [SMILES: Nc1nc(-c2ccccc2)cc(-c2ccc(OCc3ccccc3)c(F)c2F)n1] | 4-(4-(benzyloxy)-2,3-difluorophenyl)-6-phenylpyrimidin-2-amine |
| 13 | 1m | 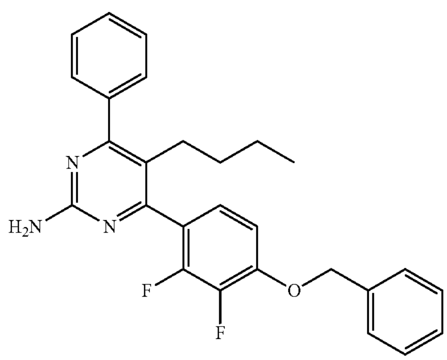 [SMILES: CCCCc1c(-c2ccccc2)nc(N)nc1-c1ccc(OCc2ccccc2)c(F)c1F] | 4-(4-(benzyloxy-2,3-difluorophenyl)-5-butyl-6-phenylpyrimidin-2-amine |
| 14 | 1n | 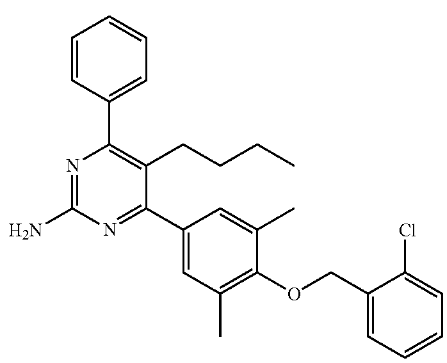 [SMILES: CCCCc1c(-c2ccccc2)nc(N)nc1-c1cc(C)c(OCc2ccccc2Cl)c(C)c1] | 5-butyl-4-(4-((2-chlorobenzyl)oxy)-3,5-dimethylphenyl)-6-phenylpyrimidin-2-amine |
| 15 | 1o | 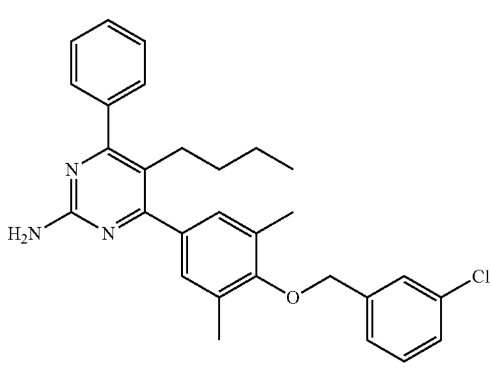 [SMILES: CCCCc1c(-c2ccccc2)nc(N)nc1-c1cc(C)c(OCc2cccc(Cl)c2)c(C)c1] | 5-butyl-4-(4-((3-chlorobenzyl)oxy)-3,5-dimethylphenyl)-6-phenylpyrimidin-2-amine |

TABLE 1-continued
Overview of the compounds prepared in following examples.
| Compound | | Structure | Nomenclature |
|---|---|---|---|
| 16 | 2a | 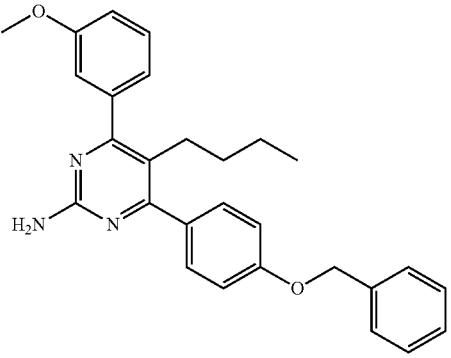 [SMILES: CCCCc1c(-c2ccc(OCc3ccccc3)cc2)nc(N)nc1-c1cccc(OC)c1] | 4-(4-(benzyloxy)phenyl)-5-butyl-6-(3-methoxyphenyl)pyrimidin-2-amine |
| 17 | 2b | 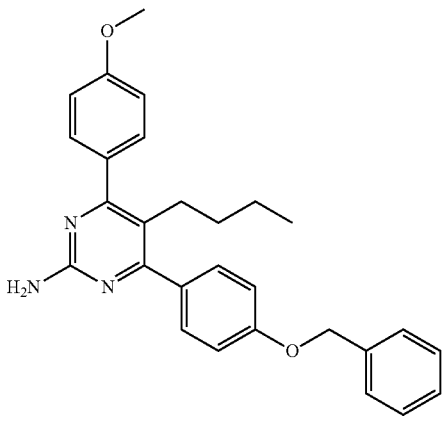 [SMILES: CCCCc1c(-c2ccc(OC)cc2)nc(N)nc1-c1ccc(OCc2ccccc2)cc1] | 4-(4-(benzyloxy)phenyl)-5-butyl-6-(4-methoxyphenyl)pyrimidin-2-amine |
| 18 | 2c | 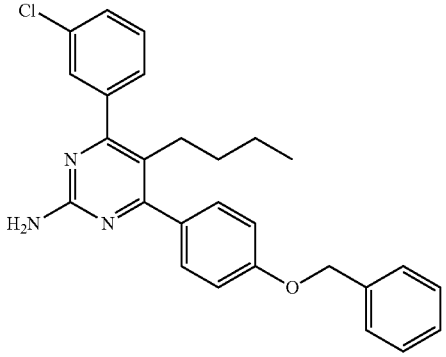 [SMILES: CCCCc1c(-c2ccc(OCc3ccccc3)cc2)nc(N)nc1-c1cccc(Cl)c1] | 4-(4-(benzyloxy)phenyl)-5-butyl-6-(3-chlorophenyl)pyrimidin-2-amine |

TABLE 1-continued

Overview of the compounds prepared in following examples.

| Compound | | Structure | Nomenclature |
|---|---|---|---|
| 19 | 2d | (structure) | 4-(4-(benzyloxy)phenyl)-5-butyl-6-(4-chlorophenyl)pyrimidin-2-amine |

Example 1

5-butyl-4-(4-ethoxyphenyl)-6-phenylpyrimidin-2-amine (1a)

The water-dioxane mixture was bubbled with argon for 5 minutes. The starting materials 5-butyl-4-chloro-6-phenylpyrimidin-2-amine (100 mg, 0.38 mmol, 1 equivalent, synthesized according to Jansa, P. WO2012116666 2012, A1), 4-ethoxyphenylboronic acid (88 mg, 0.53 mmol, 1.4 equivalent), Pd[P(Ph)$_3$]$_4$ (11 mg, 9.50 mmol, 0.025 equivalent) and Cs$_2$CO$_3$ (310 mg, 0.95 mmol, 2.5 equivalent) were added. The reaction mixture was stirred at 110° C. for 16 hours. The solvents were evaporated in vacuo. The crude reaction mixture was co-distilled twice with ethanol and purified via silica gel column chromatography (eluent cyclohexane-ethyl acetate, gradient 0 to 60%). The product was obtained as white amorphous solid (yield 83 mg, 63%).

$^1$H NMR (400 MHz, DMSO-d$_6$) δ 7.50-7.42 (m, 7H, ArH); 7.03-6.98 (m, 2H, ArH); 6.47 (s, 2H, NH$_2$); 4.08 (q, J=7.0 Hz, 2H, O—CH$_2$—CH$_3$); 1.36 (t, J=7.0 Hz, 3H, O—CH$_2$—CH$_3$); 1.02-0.92 (m, 2H, CH$_2$—CH$_2$—CH$_2$); 0.90-0.79 (m, 2H, CH$_2$—CH$_2$—CH$_3$); 0.47 (t, J=7.3 Hz, 3H, CH$_2$—CH$_3$). $^{13}$C NMR (100 MHz, DMSO-d$_6$) δ 168.04; 167.60; 161.48; 158.97; 140.25; 132.30; 130.20; 128.65; 128.42; 118.57; 114.23; 63.53; 32.18; 27.02; 22.02; 15.11; 13.63. HRMS (ESI) m/z [M+H]$^+$ calculated: C$_{22}$H$_{26}$N$_3$O 348.2070; found: 348.2071.

Example 2

5-butyl-4-(4-isopropoxyphenyl)-6-phenylpyrimidin-2-amine (1b)

Compound 1b was prepared according to the procedure in Example 1 front 5-butyl-4-chloro-6-phenylpyrimidin-2-amine (100 mg, 0.38 mmol, 1 equivalent) and 4-isopropoxyphenylboronic acid (95 mg, 0.53 mmol, 1.4 equivalent) as a white amorphous solid (yield 114 mg, 83%).

$^1$H NMR (400 MHz, DMSO-d$_6$) δ 7.50-7.40 (m, 7H, ArH); 7.02-6.96 (m, 2H, ArH); 6.46 (s, 2H, NH$_2$); 4.69 (p, J=6.0 Hz, 1H, OCH—(CH$_3$)$_2$); 1.30 (d, J=6.0 Hz, 6H, OCH—(CH$_3$)$_2$); 1.03-0.92 (m, 2H, CH$_2$—CH$_2$—CH$_2$); 0.90-0.80 (m, 2H, CH$_2$—CH$_2$—CH$_3$); 0.47 (t, J=7.3 Hz, 3H, CH$_2$—CH$_3$). $^{13}$C NMR (100 MHz, DMSO-d$_6$) δ 168.02; 167.61; 161.48; 157.91; 140.26; 132.17; 130.23; 128.64; 128.42; 118.57; 115.41; 69.66; 32.18; 27.00; 22.26; 22.02; 13.59. HRMS (ESI) m/z [M+H]$^+$ calculated: C$_{23}$H$_{28}$N$_3$O 362.2227; found: 362.2227.

Example 3

5-butyl-4-phenyl-6-(3,4,5-trimethoxyphenyl)pyrimidin-2-amine (1c)

Compound 1c was prepared according to the procedure in Example 1 from 5-butyl-4-chloro-6-phenylpyrimidin-2-amine (300 mg, 1.15 mmol, 1 equivalent) and 3,4,5-trimethoxyphenylboronic acid (341 mg, 1.61 mmol, 1.4 equivalent) as a white amorphous solid (yield 336 mg, 74%).

$^1$H NMR (400 MHz, DMSO-d6) δ 7.51-7.39 (m, 5H, ArH); 6.77 (s, 2H, ArH); 6.51 (s, 2H, NH2); 3.80 (s, 6H, m-OCH3); 3.71 (s, 3H, p-OCH3); 2.49-2.45 (m, 2H, HetAr—CH2—CH2); 1.08-0.97 (m, 2H, CH2—CH2—CH2); 0.94-0.83 (m, 2H, CH2—CH2—CH3); 0.49 (t, J=7.3 Hz, 3H, CH2—CH3); $^{13}$C NMR (100 MHz, DMSO-d6) δ 168.10; 167.85; 161.41; 152.94; 140.16; 137.89; 135.60; 128.69; 128.58; 128.43; 118.64; 106.19; 60.63; 56.47; 32.37; 27.19; 22.17; 13.62. HRMS (ESI) m/z [M+H]$^+$ calculated: C$_{23}$H$_{28}$N$_3$O$_3$ 394.2125; found: 394.2126.

Example 4

4-(4-(benzyloxy)phenyl)-6-phenylpyrimidin-2-amine (1d)

Compound 1d was prepared according to the procedure in Example 1 from 4-chloro-6-phenylpyrimidin-2-amine (100 mg, 0.49 mmol, 1 equivalent) and 4-benzyloxyphenylboronic acid (157 mg, 0.69 mmol, 1.4 equivalent) as a white amorphous solid (yield 97 mg, 56%).

$^1$H NMR (400 MHz, DMSO-d$_6$) δ 8.25-8.18 (m, 4H, ArH); 7.66 (s, 1H, HetArH); 7.55-7.47 (m, 5H, ArH); 7.45-7.33 (m, 3H, ArH); 7.18-7.13 (m, 2H, ArH); 6.67 (s, 2H, NH$_2$); 5.21 (s, 2H, O—CH$_2$—Ar). $^{13}$C NMR (100 MHz, DMSO-d$_6$) δ 165.00; 164.82; 164.37; 160.78; 137.94;

137.30; 130.78: 130.29; 129.02; 128.93; 128.39; 128.25; 127.39; 115.24; 101.54; 69.82. HRMS (EI) m/z calculated: C$_{23}$H$_{19}$N$_3$O 353.1528; found: 353.1526.

Example 5

4-(4-(benzyloxy)phenyl)-5-butyl-6-phenylpyrimidin-2-amine (1e)

Compound 1e was prepared according to the procedure in Example 1 from 5-butyl-4-chloro-6-phenylpyrimidin-2-amine (300 mg, 1.15 mmol, 1 equivalent) and 4-benzyloxyphenylboronic acid (367 mg, 1.61 mmol, 1.4 equivalent) as a white amorphous solid (yield 97 mg, 56%).

$^1$H NMR (400 MHz, DMSO-d$_6$) δ 7.51-7.31 (m, 12H, ArH); 7.13-7.07 (m, 2H, ArH); 6.47 (s, 2H, NH$_2$); 5.17 (s, 2H, O—CH$_2$—Ar); 1.02-0.92 (m, 2H, CH$_2$—CH$_2$—CH$_2$), 0.90-0.78 (m, 2H, CH$_2$—CH$_2$—CH$_3$); 0.47 (t, J=7.3 Hz, 3H, CH$_2$—CH$_3$). $^{13}$C NMR (100 MHz, DMSO-d$_6$) δ 168.06; 167.54; 161.48; 158.78; 140.24; 137.40; 132.67; 130.20; 128.90; 128.64; 128.42; 128.32; 128.21; 118.59; 114.71; 69.71; 32.20; 27.03; 22.03; 13.63. HRMS (ESI) m/z [M+H]$^+$ calculated: C$_{27}$H$_{28}$N$_3$O 410.2227; found: 410.2229.

Example 6

5-butyl-4-(4-(naphthalen-1-ylmethoxy)phenyl)-6-phenylpyrimidin-2-amine (1f)

Compound 1f was prepared according to the procedure in Example 1 from 5-butyl-4-chloro-6-phenylpyrimidin-2-amine (200 mg, 0.76 mmol, 1 equivalent) and 4-(naphthalen-1-ylmethoxy)phenylboronic acid (295 mg, 1.06 mmol, 1.4 equivalent) as a white amorphous solid (yield 125 mg, 36%).

$^1$H NMR (400 MHz, DMSO-d$_6$) δ 8.28-8.23 (m, 1H, ArH); 7.92-7.87 (m, 1H, ArH); 7.66 (d, J=8.2 Hz, 2H, ArH); 7.58-7.40 (m, 11H, ArH); 7.10 (dd, J=7.7, 1.0 Hz, 1H, ArH): 6.53 (s, 2H, NH$_2$); 5.41 (s, 2H, O—CH$_2$—Napht); 1.03-0.93 (m, 2H, CH$_2$—CH$_2$CH$_2$); 0.89-0.79 (m, 2H, CH$_2$—CH$_2$—CH$_3$); 0.45 (t, J=7.3 Hz, 3H, CH$_2$—CH$_3$). $^{13}$C NMR (100 MHz, DMSO-d$_6$) δ 168.12; 167.79; 161.49; 154.08; 140.08; 139.61; 137.65; 134.54; 128.89; 128.72; 128.63; 128.46; 127.98; 127.48; 126.95; 126.60; 125.89; 125.52; 121.99; 120.68; 118.66; 106.41; 69.66; 32.25; 26.92; 22.02; 13.55. HRMS (ESI) [M+H]$^+$ m/z calculated C$_{31}$H$_{30}$N$_3$O 460.2383; found: 460.2383.

Example 7

4-(4-4(4-methoxybenzyl)oxy)phenyl)-6-phenylpyrimidin-2-amine (1g)

Compound 1g was prepared according to the procedure in Example 1 from 4-chloro-6-phenylpyrimidin-2-amine (200 mg, 0.98 mmol, 1 equivalent) and 4-(4-methoxybenzyl)oxy) phenylboronic acid (354 mg, 1.37 mmol, 1.4 equivalent) as a white amorphous solid (yield 165 mg, 44%).

$^1$H NMR (400 MHz, DMSO-d$_6$) δ 8.30-8.15 (m, 2H, ArH); 7.85 (t, J=2.7, 1.6 Hz, 1H, ArH); 7.81 (d, J=7.6, 1.2 Hz, 1H, ArH); 7.71 (s, 1H, HetArH); 7.56-7.50 (m, 3H, ArH); 7.47-7.40 (m, 3H, ArH); 7.16 (dd, J=8.1, 2.6, 0.9 Hz, 1H, ArH); 7.01-6.94 (m, 2H, ArH); 6.75 (s, 2H, NH$_2$); 5.13 (s, 2H, CH$_2$); 3.77 (s, 3H, CH$_3$). $^{13}$C NMR (100 MHz, DMSO-d$_6$) δ 165.34; 165.05; 164.41; 159.21; 139.29; 137.79; 130.90; 130.12; 129.32; 129.05; 127.47; 119.90; 117.31; 114.30; 113.74; 102.41; 69.64; 55.57. HRMS (EI) m/z calculated: C$_{24}$H$_{22}$ON$_3$ 384.17065; found: 384.17077.

Example 8

5-butyl-4-(4-((4-methoxybenzyl)oxy)phenyl)-6-phenylpyrimidin-2-amine (1h)

Compound 1h was prepared according to the procedure in Example 1 from 5-butyl-4-chloro-6-phenylpyrimidin-2-amine (200 mg, 0.76 mmol, 1 equivalent) and 4-((4-methoxybenzyl)oxy)phenylboronic acid (274 mg, 1.06 mmol, 1.4 equivalent) as a white amorphous solid (yield 261 mg, 78%).

$^1$H NMR (400 MHz, DMSO-d$_6$) δ 7.50-7.38 (m, 9H, ArH); 7.11-7.06 (m, 2H, ArH); 6.98-6.94 (m, 2H, ArH); 6.47 (s, 2H, NH$_2$); 5.08 (s, 2H, O—CH$_2$—Ar); 3.77 (s, 3H, OCH$_3$); 1.02-0.91 (m, 2H, CH$_2$—CH$_2$—CH$_2$); 0.90-0.79 (m, 2H, CH$_2$—CH$_2$—CH$_3$); 0.47 (t, J=7.3 Hz, 3H, CH$_2$—CH$_3$). $^{13}$C NMR (100 MHz, DMSO-d$_6$) δ 168.05; 167.55; 161.46; 159.48; 158.84; 140.24; 132.54; 130.17; 130.05; 129.23; 128.64; 128.42; 118.58; 114.73; 114.28; 69.50; 55.57; 32.19; 27.03; 22.03; 13.63. HRMS (EI) m/z calculated: C$_{28}$H$_{29}$N$_3$O$_2$ 439.2260; found: 439.2266.

Example 9

4-(4-((4-chlorobenzyl)oxy)phenyl)-6-phenylpyrimidin-2-amine (1i)

Compound 1i was prepared according to the procedure in Example 1 from 4-chloro-6-phenylpyrimidin-2-amine (200 mg, 0.98 mmol, 1 equivalent) and 4-((4-chlorobenzyl)oxy) phenylboronic acid (360 mg, 1.37 mmol, 1.4 equivalent) as a white amorphous solid (yield 123 mg, 32%).

$^1$H NMR (400 MHz, DMSO-d$_6$) δ 8.28-8.04 (m, 4H, ArH); 7.66 (s, 1H, HetArH); 7.58-7.37 (m, 7H, ArH); 7.15 (d, J=9.0 Hz, 2H, ArH); 6.67 (s, 2H, NH$_2$); 5.21 (s, 2H, CH$_2$). $^{13}$C NMR (100 MHz, DMSO-d$_6$) δ 165.02; 164.78; 164.37; 160.58; 137.93; 136.38; 130.78; 130.06; 129.03; 128.93; 127.39; 125.80; 124.63; 115.26; 101.56; 68.96. HRMS (EI) m/z calculated: C$_{23}$H$_{19}$ON$_3$Cl 388.112112; found: 388.12121.

Example 10

5-butyl-4-(4-((4-chlorobenzyl)oxy)phenyl)-6-phenylpyrimidin-2-amine (1j)

Compound 1j was prepared according to the procedure in Example 1 from 5-butyl-4-chloro-6-phenylpyrimidin-2-amine (200 mg, 0.76 mmol, 1 equivalent) and 4-((4-chlorobenzyl)oxy) phenylboronic acid (278 mg, 1.06 mmol, 1.4 equivalent) as a white amorphous solid (yield 241 mg, 71%).

$^1$H NMR (400 MHz, DMSO-d$_6$) δ 7.53-7.41 (m, 11H, ArH); 7.12-7.07 (m, 2H, ArH); 6.47 (s, 2H, NH$_2$); 5.18 (s, 2H, O—CH$_2$—Ar); 1.01-0.91 (m, 2H, CH$_2$—CH$_2$—CH$_2$); 0.89-0.78 (m, 2H, CH$_2$—CH$_2$—CH$_3$); 0.46 (t, J=7.3 Hz, 3H, CH$_2$—CH$_3$). $^{13}$C NMR (100 MHz, DMSO-d$_6$) δ 168.06; 167.51; 161.47; 158.55; 140.22; 136.47; 132.89; 132.80; 130.21; 130.03; 128.90; 128.64; 128.43; 118.59; 114.77; 68.85; 32.18; 27.01; 22.03; 13.1. HRMS (EI) m/z calculated: C$_{27}$H$_{26}$N$_3$OCl 443.1764; found: 443.1768.

Example 11

4-(4-(benzyloxy)-2-methylphenyl)-5-butyl-6-phenylpyrimidin-2-amine (1k)

Compound 1k was prepared according to the procedure in Example 1 from 5-butyl-4-chloro-6-phenylpyrimidin-2-amine (100 mg, 0.38 mmol, 1 equivalent) and 4-(4-(benzyloxy)-2-methylphenylboronic acid (129 mg, 0.53 mmol, 1.4 equivalent) as a white amorphous solid (yield 137 mg, 85%).
$^1$H NMR (400 MHz, DMSO-d$_6$) δ 7.50-7.31 (m, 10H, ArH); 7.13 (d, J=8.4 Hz, 1H, ArH); 6.97 (d, J=2.5 Hz, 1H, ArH); 6.90 (dd, J=8.4, 2.6 Hz, 1H, ArH); 6.47 (s, 2H, NH$_2$); 5.14 (s, 2H, O—CH$_2$—Ar); 2.13 (s, 3H, CH$_3$—Ar); 1.00-0.89 (m, 2H, CH$_2$—CH$_2$—CH$_2$); 0.86-0.76 (m, 2H, CH$_2$—CH$_2$—CH$_3$); 0.44 (t, J=7.3 Hz, 3H, CH$_2$—CH$_3$). $^{13}$C NMR (100 MHz, DMSO-d$_6$) δ 168.51; 167.68; 161.58; 158.25; 140.08; 137.55; 136.68; 132.29; 129.70; 128.87; 128.70; 128.62; 128.45; 128.25; 128.13; 119.42; 116.57; 112.06; 69.57; 32.04; 27.01; 22.02; 19.96; 13.59. HRMS (EI) m/z calculated: C$_{28}$H$_{29}$N$_3$O 423.2311; found: 423.2314.

Example 12

4-(4-(benzyloxy)-2,3-difluorophenyl)-6-phenylpyrimidin-2-amine (1l)

Compound 1l was prepared according to the procedure in Example 1 from 4-chloro-6-phenylpyrimidin-2-amine (21 mg, 0.1 mmol, 1 equivalent) and 4-(benzyloxy)-2,3-difluorophenylboronic acid (36 mg, 0.14 mmol, 1.4 equivalent) as a white amorphous solid (yield 38 mg, 97%).
$^1$H NMR (400 MHz, DMSO-d$_6$) δ 8.13-8.08 (m, 2H, ArH); 7.79 (td, J=8.7, 2.3 Hz, 1H, ArH); 7.56-7.49 (m, 5H, ArH); 7.47-7.35 (m, 4H, ArH+HetArH); 7.34-7.27 (m, 1H, ArH); 6.84 (s, 2H, NH$_2$); 5.32 (s, 2H, O—CH$_2$—Ar). $^{13}$C NMR (100 MHz, DMSO-d$_6$) δ 165.26; 164.36; 161.10; 137.55; 136.38; 131.05; 129.21; 129.05; 128.78; 128.48; 127.31; 124.82; 110.91; 105.53; 105.45; 71.29. HRMS (EI) m/z calculated: C$_{23}$H$_{17}$N$_3$OF$_2$ 389.1340; found: 389.1345.

Example 13

4-(4-(benzyloxy)-2,3-difluorophenyl)-5-butyl-6-phenylpyrimidin-2-amine (1m)

Compound 1m was prepared according to the procedure in Example 1 from 5-butyl-4-chloro-6-phenylpyrimidin-2-amine (100 mg, 0.38 mmol, 1 equivalent) and 4-(benzyloxy)-2,3-difluorophenylboronic acid (140 mg, 0.53 mmol, 1.4 equivalent) as a white amorphous solid (yield 42 mg, 25%).
$^1$H NMR (400 MHz, DMSO-d$_6$) δ 7.52-7.34 (m, 10H, ArH); 7.24-7.20 (m, 2H, ArH); 6.64 (s, 2H, NH$_2$); 5.30 (s, 2H, O—CH$_2$—Ar); 1.01-0.91 (m, 2H, CH$_2$—CH$_2$—CH$_2$); 0.90-0.79 (m, 2H, CH$_2$—CH$_2$—CH$_3$); 0.45 (t, J=7.2 Hz, 3H, CH$_2$—CH$_3$). $^{13}$C NMR (100 MHz, DMSO-d$_6$) δ 168.10; 162.16; 162.13; 161.69; 139.68; 136.48; 129.01; 128.90; 128.70; 128.57; 128.53; 128.41; 124.97; 124.92; 121.59; 121.45; 119.90; 111.12; 71.27; 32.12; 27.00; 21.92; 13.54. HRMS (EI) m/z calculated: C$_{27}$H$_{25}$N$_3$OF$_2$ 445.1966; found: 445.1964.

Example 14

5-butyl-4-(4-((2-chlorobenzyl)oxy)-3,5-dimethylphenyl)-6-phenylpyrimidin-2-amine (1n)

Compound 1n was prepared according to the procedure in Example 1 from 5-butyl-4-chloro-6-phenylpyrimidin-2-amine (200 mg, 0.76 mmol, 1 equivalent) and 4-((2-chlorobenzyl)oxy)-3,5-dimethylphenylboronic acid (308 mg, 1.06 mmol, 1.4 equivalent) as a white amorphous solid (yield 349 mg, 97%).
$^1$H NMR (400 MHz, DMSO-d$_6$) δ 7.69-7.65 (m, 1H, ArH); 7.56-7.51 (m, 1H, ArH); 7.50-7.41(m, 7H, ArH); 7.19 (s, 2H, ArH); 6.48 (s, 2H, NH$_2$); 4.96 (s, 2H, O—CH$_2$—Ar); 2.27 (s, 6H, Ar—CH$_3$); 1.05-0.94 (m, 2H, CH$_2$—CH$_2$—CH$_2$); 0.94-0.81 (m, 2H, CH$_2$—CH$_2$—CH$_3$), 0.50 (t, J=7.3 Hz, 3H, CH$_2$—CH$_3$). $^{13}$C NMR (100 MHz, DMSO-d$_6$) δ 168.04; 167.66; 161.44; 155.50; 140.21; 135.85; 135.28; 133.12; 131.06; 130.69; 130.45; 129.80; 129.27; 128.66; 128.62; 128.44; 127.88; 118.57; 71.16; 32.23; 26.96; 22.02; 16.57; 13.56. HRMS (ESI) [M+H]$^+$ m/z calculated: C$_{29}$H$_{31}$N$_3$OCl 472.2150; found: 472.2150.

Example 15

5-butyl-4-(4-((3-chlorobenzyl)oxy)-3,5-dimethylphenyl)-6-phenylpyrimidin-2-amine (1o)

Compound 1o was prepared according to the procedure in Example 1 from 5-butyl-4-chloro-6-phenylpyrimidin-2-amine (200 mg, 0.76 mmol, 1 equivalent) and 44(3-chlorobenzyl)oxy)-3,5-dimethylphenylboronic acid (308 mg, 1.06 mmol, 1.4 equivalent) as a white amorphous solid (yield 336 mg, 94%).
$^1$H NMR (400 MHz, DMSO-d$_6$) δ 7.52-7.41 (m, 9H, ArH); 7.20 (s, 2H, ArH); 6.48 (s, 2H, NH$_2$); 4.89 (s, 2H, O—CH$_2$—Ar); 2.28 (s, 6H, Ar—CH$_3$); 1.06-0.95 (m, 2H, CH$_2$—CH$_2$—CH$_2$); 0.94-0.82 (m, 2H, CH$_2$—CH$_2$—CH$_3$); 0.50 (t, J=7.3 Hz, 3H, CH$_2$—CH$_3$). $^{13}$C NMR (100 MHz, DMSO-d$_6$) δ 168.05; 167.65; 161.44; 155.50; 140.48; 140.21; 135.82; 133.48; 130.81; 130.63; 129.29; 128.67; 128.61; 128.44; 128.30; 128.02; 126.93; 118.56; 72.88; 32.22; 26.96; 22.01; 16.63; 13.57. HRMS (ESI) [H+H]$^+$ m/z calculated: C$_{29}$H$_{31}$N$_3$OCl 472.2150; found: 472.2150.

Example 16

4-(4-(benzyloxy)phenyl)-5-butyl-6-(3-methoxyphenyl)pyrimidin-2-amine (2a)

Compound 2a was prepared according to the procedure in Example 1 from 4-(4-(benzyloxy)phenyl)-5-butyl-6-chloropyrimidin-2-amine (200 mg, 0.54 mmol, 1 equivalent) and 3-methoxyphenylboronic acid (148 mg, 0.97 mmol, 1.8 equivalent) as a white amorphous solid (yield 132 mg, 56%).
$^1$H NMR (400 MHz, DMSO-d$_6$) δ 7.53-7.30 (m, 8H, ArH); 7.14-7.07 (m, 2H, ArH); 7.06-6.96 (m, 3H, ArH); 6.47 (s, 2H, NH$_2$); 5.17 (s, 2H, CH$_2$); 3.79 (s, 3H, CH$_3$); 1.07-0.93 (m, 2H, CH$_2$—CH$_2$—CH$_2$); 0.92-0.79 (m, 2H, CH$_2$—CH$_2$—CH$_3$); 0.49 (t, J=7.3 Hz, 3H, CH$_2$—CH$_3$). $^{13}$C NMR (100 MHz, DMSO-d$_6$) δ 167.84; 167.55; 161.44; 159.30; 158.77; 141.59; 137.40; 132.67; 130.19; 129.59; 128.90; 128.32; 128.21; 120.93; 118.58; 114.71; 69.71; 55.65; 32.24; 27.08; 22.07; 13.66. HRMS (EI) m/z calculated: C$_{28}$H$_{30}$O$_2$N$_3$ 440.23325; found: 440.23321.

Example 17

4-(4-(benzyloxy)phenyl)-5-butyl-6-(4-methoxyphenyl)pyrimidin-2-amin (2b)

Compound 2b was prepared according to the procedure in Example 1 from 4-(4-(benzyloxy)phenyl)-5-butyl-6-chloropyrimidin-2-amine (200 mg, 0.54 mmol, 1 equivalent) a 4-methoxyphenylboronic acid (148 mg, 0.97 mmol, 1.8 equivalent) as a white amorphous solid (yield 161 mg, 68%).

$^1$H NMR (400 MHz, DMSO-$d_6$) δ 7.52-7.30 (m, 9H, ArH) 7.14-7.07 (m, 2H, ArH); 7.06-6.97 (m, 2H, ArH); 6.41 (s, 2H, NH$_2$); 5.17 (s, 2H, CH$_2$); 3.81 (s, 3H, CH$_3$); 2.60-2.53 (m, 2H, HetAr—CH$_2$—CH$_2$); 1.02-0.92 (m, 2H, CH$_2$—CH$_2$—CH$_2$); 0.91-0.80 (m, 2H, CH$_2$—CH$_2$—CH$_3$); 0.49 (t, J=7.3 Hz, 3H, CH$_2$—CH$_3$). $^{13}$C NMR (100 MHz, DMSO-$d_6$) δ 167.56; 161.47; 159.66; 158.73; 137.41; 132.83; 130.22; 128.89; 128.32; 128.21; 118.57; 114.69; 113.77; 69.70; 55.61; 32.13; 27.13; 22.02; 13.70. HRMS (EI) m/z calculated: $C_{28}H_{30}O_2N_3$ 440.23325; found: 440.23322.

Example 18

4-(4-(benzyloxy)phenyl)-5-butyl-6-(3-chlorophenyl)pyrimidin-2-amine (2c)

Compound 2c was prepared according to the procedure in Example 1 from 4-(4-(benzyloxy)phenyl)-5-butyl-6-chloropyrimidin-2-amine (200 mg, 0.54 mmol, 1 equivalent) a 3-chlorophenylboronic acid (152 mg, 0.97 mmol, 1.8 equivalent) as a white amorphous solid (yield 145 mg, 61%).

$^1$H NMR (400 MHz, DMSO-$d_6$) δ 7.59-7.28 (m, 8H, ArH); 7.10 (d, J=8.7 Hz, 2H, ArH); 6.55 (s, 2H, NH$_2$); 5.17 (s, 2H, CH$_2$), 0.97 (d, J=7.9 Hz, 2H, CH$_2$—CH$_2$—CH$_2$); 0.87 (q, J=7.1 Hz, 2H, CH$_2$—CH$_2$—CH$_3$); 0.49 (t, J=7.2 Hz, 3H, CH$_2$—CH$_3$). $^{13}$C NMR (100 MHz, DMSO-$d_6$) δ 167.85 166.36; 116.15; 158.86; 142.23; 137.38; 133.21; 132.49; 130.45; 13022; 128.90; 128.65; 128.58; 128.33; 128.22; 127.44; 118.56; 114.74; 69.72; 32.14; 26.96; 21.99; 13.60.

HRMS (EI) m/z calculated: $C_{27}H_{27}ON_3Cl$ 444.18372; found: 444.18375.

Example 19

4-(4-(benzyloxy)phenyl)-5-butyl-6-(4-chlorophenyl)pyrimidin-2-amine (2d)

Compound 2d was prepared according to the procedure in Example 1 from 4-(4-(benzyloxy)phenyl)-5-butyl-6-chloropyrimidin-2-amine (200 mg, 0.54 mmol, 1 equivalent) a 4-chlorophenylboronic acid (152 mg, 0.97 mmol, 1.8 equivalent) as a white amorphous solid (yield 148 mg, 62%).

$^1$H NMR (400 MHz, DMSO-$d_6$) δ 7.66-7.20 (m, 12H, ArH); 7.17-7.04 (m, 2H, ArH); 6.53 (s, 2H, NH$_2$); 5.17 (s, 2H, CH$_2$); 1.02-0.91 (m, 2H, CH$_2$—CH$_2$—CH$_2$); 0.91-0.79 (m, 2H, CH$_2$—CH$_2$—CH$_3$); 0.49 (t, J=7.2 Hz, 3H, CH$_2$—CH$_3$). $^{13}$C NMR (100 MHz, DMSO-$d_6$) δ 167.78; 166.74; 161.50; 158.83; 139.05; 137.39; 133.44; 132.54; 130.66; 130.21; 128.90; 128.54; 128.33; 128.22; 118.57; 114.73; 69.72; 32.16; 26.99; 22.00; 13.64. HRMS (EI) m/z calculated: $C_{27}H_{27}ON_3Cl$ 444.18372; found: 444.18367.

Results of Biological Assays

Production of PGE$_2$ was assayed in vitro in cultures of mouse peritoneal cells. The cells ($2\times10^6$/mL) were stimulated with bacterial lipopolysaccharide (LPS, 10 ng/ml). Tested pyrimidine derivatives were applied at the concentration of 50 μmol.l$^{-1}$, concomitantly with LPS. Amount of PGE$_2$ in cell supernatants was determined 5 hours after stimulation using the commercially available kit (R&D Systems). The effects of pyrimidines on PGE$_2$ production were evaluated in percent of control values, i.e. those found after the action of LPS alone (100%). The data in Table 2 show the remaining activity; the low values thus indicate strong inhibition of PGE$_2$ formation.

The concentrations required to inhibit PGE$_2$ biosynthesis by 50% (so-called IC$_{50}$) were determined by the analysis of concentration-effect experiments. For this purpose, the compounds were applied within the range of 0.0004 μmol.l$^{-1}$ až 25 μmol.l$^{-1}$.

Cell viability was determined using the lactate dehydrogenase assay (LDH kit, Sigma-Aldrich). The mouse peritoneal cells were cultured for 5 hours in the presence of tested compounds applied at the concentration of 50 μmol.l$^{-1}$. The effects of pyrimidines were compared with the viability of cells cultured in the absence of the compounds. The later was taken as a control 100% viability. As a rule, the compounds did not exhibit any significant cytotoxicity. The only exception was 16 (2a), which reduced the viability to 43.1% of controls.

TABLE 2

Effect of tested pyrimidine derivatives (50 μmol · l$^{-1}$) on the biosynthesis of PGE$_2$ and viability of cells

| | | PGE$_2$ | | |
| --- | --- | --- | --- | --- |
| Example | Compound | remaining activity in % of LPS response (mean ± SEM) | IC$_{50}$ (μmol · l$^{-1}$), and 95% limits of confidence (in parentheses) | Cell viability in % of untreated controls (LDH assay) |
| 1 | 1a | 26.3 ± 0.1 (n = 8) | not determined | 104.6 ± 1.3 (n = 8) |
| 2 | 1b | 12.3 ± 0.5 (n = 8) | not determined | 71.2 ± 1.9 (n = 8) |
| 3 | 1c | 10.1 ± 2.6 (n = 8) | not determined | 102.6 ± 0.6 (n = 8) |
| 4 | 1d | 0.7 ± 0.8 (n = 2) | not determined | 101.2 ± 0.7 (n = 4) |
| 5 | 1e | 0.3 ± 0.1 (n = 8) | 0.094 (0.045-0.197) | 105.4 ± 0.2 (n = 8) |
| 6 | 1f | 26.3 ± 5.3 (n = 4) | not determined | 104.8 ± 0.4 (n = 8) |
| 7 | 1g | 8.4 ± 3.0 (n = 2) | not determined | 99.6 ± 3.0 (n = 4) |
| 8 | 1h | 2.0 ± 1.5 (n = 4) | 5.40 (3.89-7.50) | 104.2 ± 0.3 (n = 8) |
| 9 | 1i | 15.4/1.1 (n = 2) | not determined | 102.2 ± 4.1 (n = 4) |
| 10 | 1j | 0.7 ± 0.5 n = 4) | 0.077 (0.039-0.152) | 101.2 ± 0.8 (n = 8) |
| 11 | 1k | 51.1 ± 0.8 (n = 4) | not determined | 103.2 ± 0.5 (n = 8) |
| 12 | 1l | 5.5 ± 0.3 (n = 2) | not determined | 102.6 ± 3.7 (n = 4) |
| 13 | 1m | 0.03 ± 0.2 (n = 4) | 0.006 (0.003-0.011) | 103.7 ± 0.4 (n = 8) |
| 14 | 1n | 7.1 ± 1.9 (n = 4) | not determined | 103.6 ± 0.3 (n = 8) |
| 15 | 1o | 6.5 ± 0.4 (n = 4) | not deteriminded | 102.8 ± 0.4 (n = 8) |
| 16 | 2a | 10.0 ± 2.0 (n = 2) | not determined | 43.1 ± 8.4 (n = 4) |
| 17 | 2b | 10.5 ± 0.1 (n = 2) | not determined | 100.3 ± 1.2 (n = 4) |
| 18 | 2c | 12.6 ± 1.7 (n = 2) | not determined | 101.3 ± 2.0 (n = 4) |
| 19 | 2d | 4.1 ± 0.7 (n = 2) | not determined | 96.7 ± 2.2 (n = 4) |

Similar to the PGE$_2$ assay, the production of nitric oxide (NO) was followed under conditions in vitro using murine peritoneal cells (FIG. 1). The cells ($2\times10^6$/ml) were cultured in presence of lipopolysaccharide (LPS, 0.1 ng/ml) and recombinant mouse interferon-γ (IFN-γ, 5 ng/ml). Effects of tested pyrimidine derivatives were screened at the concentration of 50 μmol.l$^{-1}$. The compounds were added concomitantly with LPS/IFN-γ. The concentration of nitrites in cell supernatants (a measure of NO production) was evaluated spectrophotometrically, 24 h after the priming stimuli. Griess reagent was used for this purpose. The effects of pyrimidines on NO production were evaluated in percent of control values, i.e those found after the action of LPS/IFN-γ alone (100%).

The tested pyrimidine derivatives exhibit a markedly enhanced inhibitory selectivity towards the biosynthesis of PGE$_2$ (see Table 1). Their effects on production of NO, which were assayed at the same concentration (i.e. 50 μmol.l$^{-1}$) were rather marginal (FIG. 1). This can be exemplified by compound 1m (13). While it completely inhibits PGE$_2$ production, the production of NO is lowered to 84% of controls only.

INDUSTRIAL APPLICABILITY

Due to the fact, that the pyrimidines derivatives shown here are non-toxic inhibitors of PGE$_2$ production, they can be considered as compounds suitable for the development of new medicament for the treatment of inflammatory and tumor-related diseases.

The invention claimed is:

1. Polysubstituted pyrimidines of the formula (I)

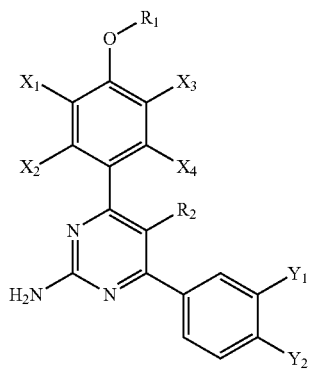

(I)

where
  X$_1$ is selected from the group consisting of —H, —F, —Cl, and alkyl;
  X$_2$ is selected from the group consisting of —H, —F, —Cl, and alkyl;
  X$_3$ is selected from the group consisting of —H, —F, —Cl, and alkyl;
  X$_4$ is selected from the group consisting of —H, —F, —Cl, and alkyl;
  Y$_1$ is selected from the group consisting of —H, —F, —Cl, and —OR, wherein R is alkyl;
  Y$_2$ is selected from the group consisting of —H, —F, —Cl, and —OR, wherein R is alkyl;
  R$_1$ is aryl as defined herein;
  R$_2$ is alkyl as defined herein;
  or a pharmaceutically acceptable salt thereof,
  wherein
  alkyl in these cases is defined as a linear or branched C$_1$-C$_{10}$ carbon chain;
  aryl in the above cases is defined as a hydrocarbon group containing 6 to 14 carbon atoms containing at least one aromatic ring, wherein the aryl may be unsubstituted or substituted with 1 to 5 substituents selected from the group of —F, —Cl, and —OR, wherein R is alkyl as defined herein.

2. Polysubstituted pyrimidines selected from the group comprising:
  4-(4-(benzyloxy)phenyl)-6-phenylpyrimidin-2-amine
  4-(4-(benzyloxy)phenyl)-5-butyl-6-phenylpyrimidin-2-amine
  5-butyl-4-(4-(naphthalen-1-ylmethoxy)phenyl)-6-phenylpyrimidin-2-amine
  4-(4-((4-methoxybenzyl)oxy)phenyl)-6-phenylpyrimidin-2-amine
  5-butyl-4-(4-((4-methoxybenzyl)oxy)phenyl)-6-phenylpyrimidin-2-amine
  4-(4-((4-chlorobenzyl)oxy)phenyl)-6-phenylpyrimidin-2-amine
  5-butyl-4-(4-((4-chlorobenzyl)oxy)phenyl)-6-phenylpyrimidin-2-amine
  4-(4-(benzyloxy)-2-methylphenyl)-5-butyl-6-phenylpyrimidin-2-amine
  4-(4-(benzyloxy)-2,3-difluorophenyl)-6-phenylpyrimidin-2-amine
  4-(4-(benzyloxy)-2,3-difluorophenyl)-5-butyl-6-phenylpyrimidin-2-amine
  5-butyl-4-(4-((2-chlorobenzyl)oxy)-3,5-dimethylphenyl)-6-phenylpyrimidin-2-amine
  5-butyl-4-(4-((3-chlorobenzyl)oxy)-3,5-dimethylphenyl)-6-phenylpyrimidin-2-amine
  4-(4-(benzyloxy)phenyl)-5-butyl-6-(3-methoxyphenyl)pyrimidin-2-amine
  4-(4-(benzyloxy)phenyl)-5-butyl-6-(4-methoxyphenyl)pyrimidin-2-amine
  4-(4-(benzyloxy)phenyl)-5-butyl-6-(3-chlorophenyl)pyrimidin-2-amine
  4-(4-(benzyloxy)phenyl)-5-butyl-6-(4-chlorophenyl)pyrimidin-2-amine
  and their pharmaceutically acceptable salts.

3. A pharmaceutical composition comprising a therapeutically effective amount of at least one compound of the formula I according to claim 1 and optionally at least one pharmaceutically acceptable carrier, filler and/or diluent and/or adjuvant.

* * * * *